(12) United States Patent
Jang et al.

(10) Patent No.: US 6,723,085 B2
(45) Date of Patent: Apr. 20, 2004

(54) ARTERIAL FILTER WITH ASPIRATION AND METHODS OF USE

(75) Inventors: Yue-Teh Jang, Fremont, CA (US); Richard O. Murphy, Sunnyvale, CA (US); Roman Turovskiy, San Francisco, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 10/174,074

(22) Filed: Jun. 17, 2002

(65) Prior Publication Data

US 2002/0161396 A1 Oct. 31, 2002

Related U.S. Application Data

(63) Continuation of application No. 09/473,584, filed on Dec. 28, 1999, now Pat. No. 6,406,471.

(51) Int. Cl.[7] .............................. A61M 1/00
(52) U.S. Cl. .................. 604/540; 604/507; 606/200
(58) Field of Search .................. 604/540, 104, 604/500, 507–510; 606/192, 194, 200

(56) References Cited

U.S. PATENT DOCUMENTS

| 4,407,271 A | 10/1983 | Schiff |
| 4,531,935 A | 7/1985 | Berryessa |
| 4,723,549 A | 2/1988 | Wholey et al. |
| 5,011,488 A | 4/1991 | Ginsburg |
| 5,053,008 A | 10/1991 | Bajaj |
| 5,282,744 A * | 2/1994 | Meyer .................. 433/92 |
| 5,846,260 A * | 12/1998 | Maahs .................. 606/200 |
| 5,865,802 A | 2/1999 | Yoon et al. |
| 6,136,016 A | 10/2000 | Barbut et al. |
| 6,179,851 B1 | 1/2001 | Barbut et al. |
| 6,406,471 B1 * | 6/2002 | Jang et al. .................. 604/540 |

* cited by examiner

Primary Examiner—Brian L. Casler
Assistant Examiner—Jeremy Thissell
(74) Attorney, Agent, or Firm—John Christopher James; O'Melveny & Myers LLP

(57) ABSTRACT

A filter comprising a porous material is arranged in a generally conical shape having an expandable base and a vertex. An elongate member having a proximal end and a distal end is attached to the expandable base of the porous material at a first circumferential location of the expandable base and extends perpendicularly from a central axis of the filter. An aspiration tube, for removing embolic material under vacuum, communicates with an area at the first circumferential location of the expandable base. Methods of using the filter and occluding devices for protecting a patient from embolization during cardiovascular procedures are described.

20 Claims, 6 Drawing Sheets

* Aspiration tube 20 now terminates just inside the vessel.

* Aspiration tube 20 now terminates just inside the vessel.

ARTERIAL FILTER WITH ASPIRATION AND METHODS OF USE

This is a continuation of U.S. application Ser. No. 09/473,584, filed Dec. 28, 1999, now U.S. Pat. No. 6,406,471, the contents of which are incorporated herein by reference in their entirety.

FIELD OF THE INVENTION

The present invention relates generally to medical devices for protecting a patient from embolization during cardiovascular procedures. More particularly, the devices comprise a filter for temporary placement in a patient's vessel, and an aspiration tube communicating with a portion of the filter, e.g., a reservoir tip at a vertex of the filter, for aspirating embolic material, including air and gas.

BACKGROUND OF THE INVENTION

Aspiration catheters are frequently used during surgical or interventional procedures for removing thromboembolic material, e.g., air, fluid, thrombi, calcium, atheromatous plaque, and/or tissue debris, from a patient's body cavity. During cardiovascular procedures, such as coronary artery bypass grafting surgery, ventricular septal defect repair, heart valve repair or replacement, ventricular myomectomy, aortic aneurysm repair, or aortic thrombectomy, removal of thromboembolic material from a cardiac chamber and/or the aorta is important since distal embolization may result in ischemia or infarction of peripheral organs, particularly the brain.

Endovascular techniques have been used widely as an effective and reliable alternative to surgical intervention in selected patients for treatment of vascular stenosis. It is well recognized that one of the complications associated with endovascular techniques is the dislodgment of embolic materials generated during manipulation of the vessel, thereby causing occlusion of the narrower vessels downstream and ischemia or infarct of the organ which the vessel supplies.

Several arterial and venous filters have been designed for entrapment of embolic debris generated during surgical or endovascular procedures. An aspiration catheter is often required for complete removal of embolic debris. Current aspiration catheters are designed to remove fluid and tissue debris in a body cavity. Removal of air, however, is difficult because the air bubbles tend to accumulate against the vessel wall at a position difficult to reach. Thus, removal of embolic material is often not complete and patients remain at risk for air embolization.

Thus, there is a need for devices and methods which are capable of capturing and effectively removing embolic material within a patient's body tissue or cavity during surgical or endovascular procedures.

SUMMARY OF THE INVENTION

The present invention provides an intravascular filter for temporary placement in a patient's vessel, such as an artery or vein. In a first embodiment, the filter comprises a porous material arranged in a generally conical shape having a base and a vertex. The base is expandable and collapsible. A reservoir tip is located at the vertex of the cone for collecting filtered embolic material. The tip also communicates with a distal end of an aspiration catheter. In certain embodiments, the reservoir tip comprises a nonporous material, e.g., latex. In other embodiments, the distal end of the aspiration tube extends only to the outer edge of the filter, e.g., the point of insertion into the vessel.

In another embodiment, the filter is mounted on a cannula, and the aspiration tube extends proximally within the cannula. The proximal end of the aspiration tube communicates with a vacuum pump.

In another embodiment, the filter is mounted on an insertion handle, and the aspiration tube extends proximally within the insertion handle. The aspiration tube includes an infusion port at the distal end for infusion of fluid, such as saline or heparin.

In another embodiment, the filter is mounted on a distal end of an obturator, and the aspiration tube extends proximally within the obturator. The distal end of the aspiration tube may further include a turbine which extends into the reservoir tip for removing large embolic particles.

The present invention further provides occluding devices for temporary placement in a patient's vessel, such as an artery or vein. In a first embodiment, the device comprises a nonporous material arranged in a conical shape having an expandable base and a vertex. A reservoir tip is located at the vertex of the cone for collecting filtered embolic material. The tip also communicates with a distal end of an aspiration catheter. In certain embodiments, the device is mounted on an insertion handle, having the aspiration tube extending proximally within the handle. Alternatively, the device is mounted on a cannula or an obturator.

The invention also provides methods for protecting a patient from embolization using the filter or occluding devices described above. During cardiopulmonary bypass, for example, the filter or the occluding device is placed in a collapsed state and inserted into the patient's aorta. The filter or the occluding device is expanded to capture embolic material, including air, fluid, thrombi, calcium, atheromatous plaque, and/or tissue debris. The proximal end of the aspiration catheter is connected to a vacuum, and emboli are aspirated under negative pressure and removed from the aorta. The filter or the occluding device is then collapsed and removed from the aorta.

It will be understood that there are several advantages associated in using the devices and methods disclosed herein for preventing embolic complication during cardiovascular procedures. For example, (1) the filter is adapted for temporary placement in a patient's artery or vein; (2) the filter communicates with an aspiration tube for removal of embolic material; (3) the filter includes capability, such as a turbine or infusion port, for breakup of large embolic particles; (4) the occluding device provides aortic occlusion during cardiopulmonary bypass in addition to providing protection from distal embolization; (5) using the occluding device in place of an aortic clamp minimizes vascular injury caused by the clamp; and (6) the devices remove air and gas in addition to particles liable to cause distal embolization.

DETAILED DESCRIPTION

Figure 1A:
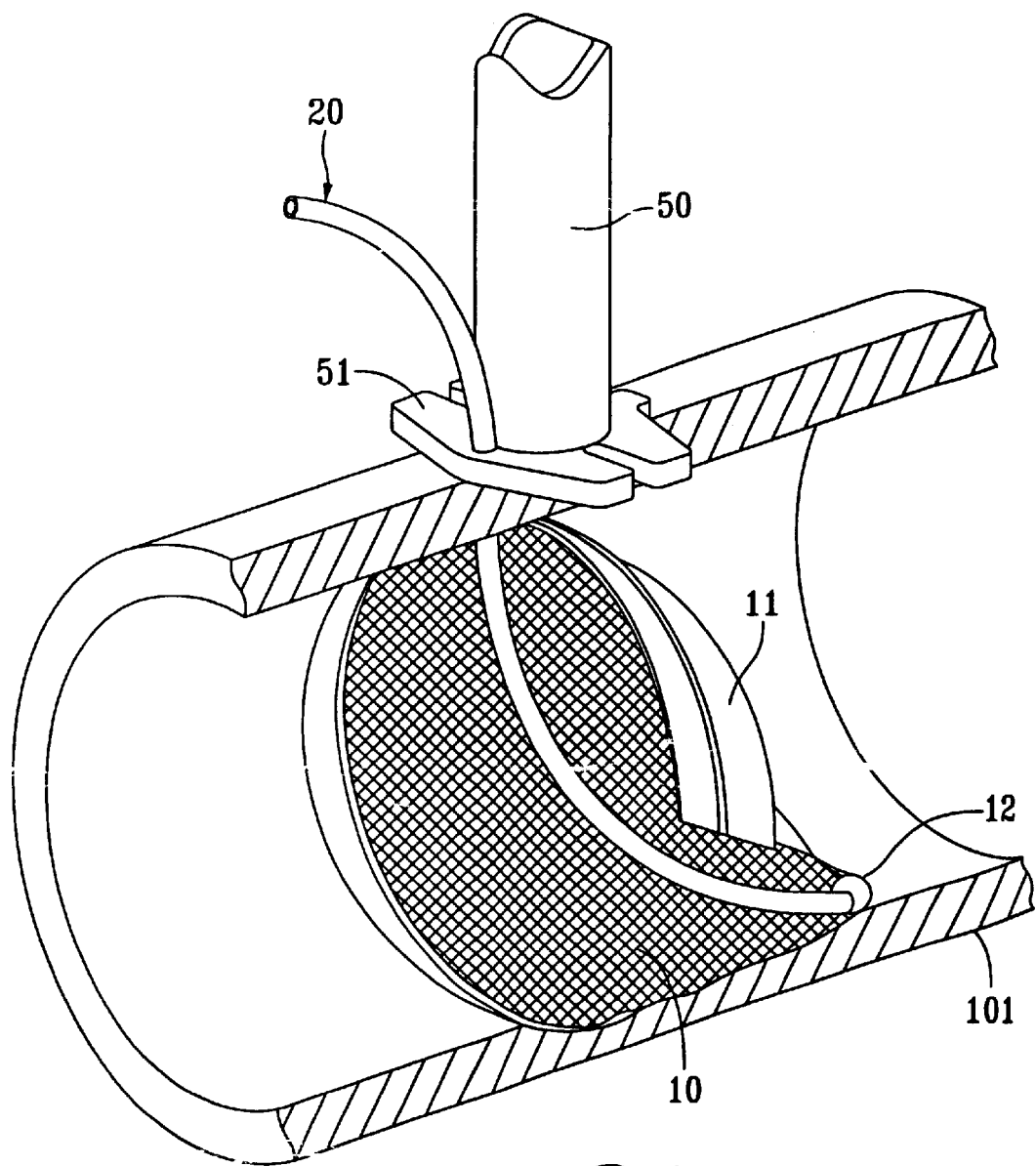
FIG. 1A depicts a filter with aspiration capabilities deployed in a vessel.
Figure 1C:
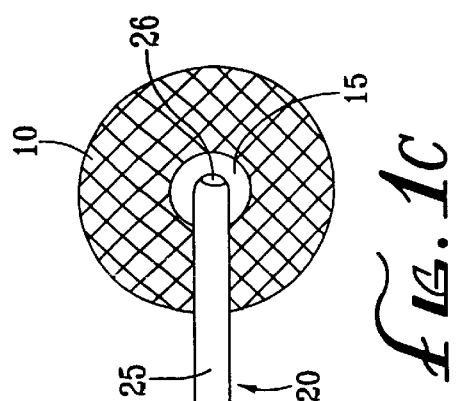
FIG. 1C depicts a distal view of the filter of FIG. 1B.
Figure 1B:
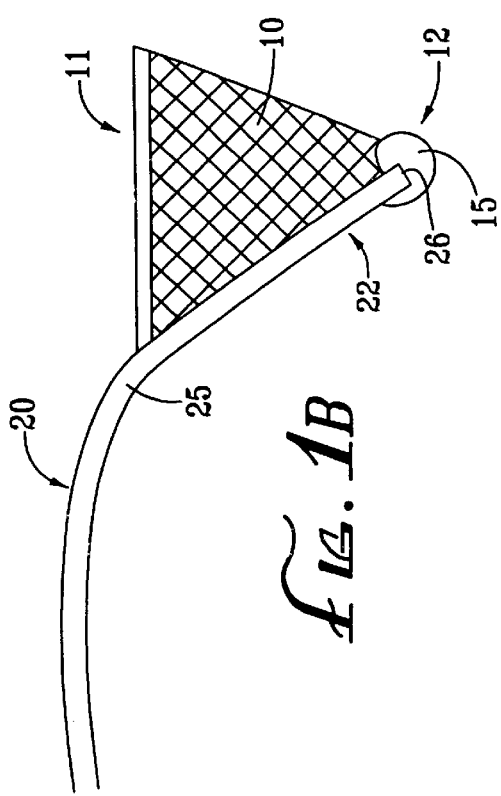
FIG. 1B depicts a lateral view of a filter having a reservoir tip communicating with an aspiration catheter.

The devices and methods disclosed herein are adapted for temporary placement in a patient's artery or vein for entrapment and removal of embolic debris. The devices are particularly useful in cardiovascular surgeries for preventing distal embolization to peripheral organs. An embodiment of the filter is depicted in FIGS. 1A, 1B, and 1C. Filter 10 comprises a porous material arranged in a conical shape having expandable base 11 and vertex 12. Reservoir tip 15 is located at vertex 12 for collecting embolic material, and communicates with distal port 26 at distal end 22 and lumen 25 of aspiration tube 20. A proximal end (not shown) of the aspiration tube is adapted for attachment to a vacuum. In this embodiment, reservoir tip 15 comprises a nonporous material, e.g., latex. In other embodiments, the reservoir tip is constructed of the same material as the filter mesh.

The construction and use of expansion means and associated filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, filed Apr. 30, 1996, Barbut et al., U.S. application Ser. No. 08/645,762, filed May 14, 1996, and Barbut et al., U.S. Pat. No. 5,662,671, and the contents of each of these prior applications are expressly incorporated herein by reference in their entirety.

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is sonic welded into a cone shape. Other meshes known in the art, which have the desired physical characteristics, are also suitable. For example, the filter may be constructed of a thin film material with laser cut holes. Anticoagulant, such as heparin and heparinoids, may be applied to the mesh to reduce the chances of blood clotting on the mesh. Anticoagulants other than heparinoids also may be used, e.g., ReoPro (Centocor). The anticoagulant may be painted or sprayed onto the mesh. A chemical dip comprising the anticoagulant also may be used. Other methods known in the art for applying chemicals to mesh may be used.

Figure 2B:
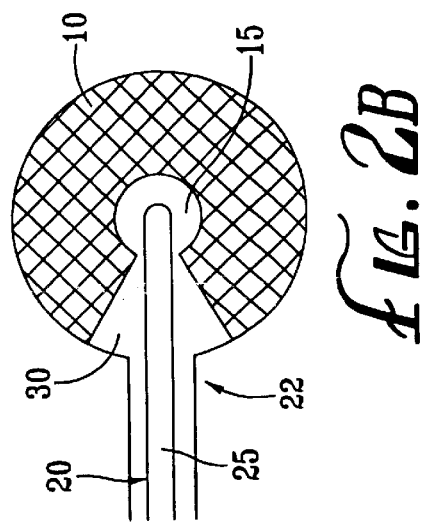
FIG. 2B depicts a distal view of the filter of FIG. 2A.
Figure 2A:
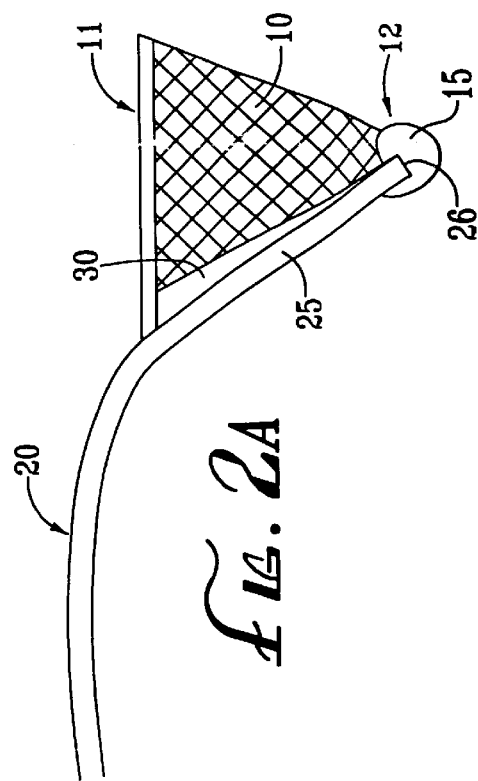
FIG. 2A depicts a lateral view of another embodiment of the filter including a conical-shaped nonporous material.

Another embodiment of the filter is depicted in FIGS. 2A and 2B. Reservoir tip 15 comprises a nonporous material, e.g., latex, which extends into a portion of filter 10 and covers area 30. Area 30 is shaped like a sector of a circle having two radii and the included arc. In certain embodiments, latex may extend to cover distal end 22 of aspiration tube 20 as shown in FIG. 2B.

Figure 3A:
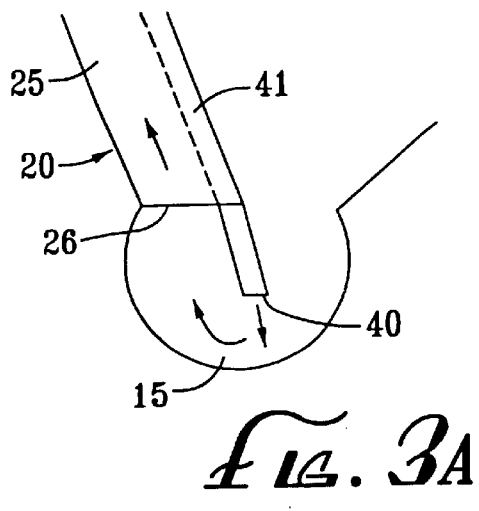
FIG. 3A depicts another embodiment of the filter having an infusion port.
Figure 3B:
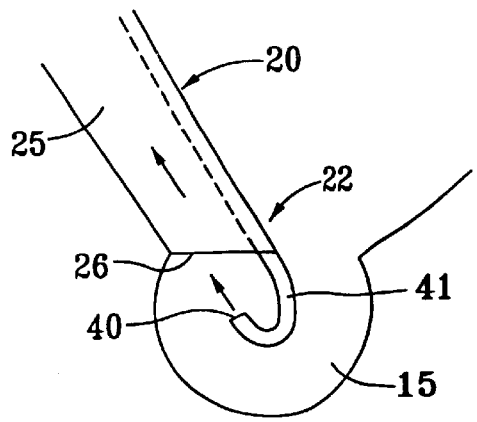
FIG. 3B depicts another embodiment of the filter having an angulated infusion port.

FIG. 3A depicts another embodiment of aspiration tube 20 having infusion port 40 at distal end 22. Infusion port 40 communicates with infusion lumen 41, which is included in the aspiration catheter. The infusion port and lumen are adapted for infusion of fluid, e.g., saline, or Ringer's lactate, for irrigating embolic material, and pharmaceutical agent, e.g., heparin or streptokinase to facilitate breakup of large thrombi dislodged within tip 15. Infusion port 40 may be angled relative to the axis of infusion lumen 41 as depicted in FIG. 3B.

Figure 4:
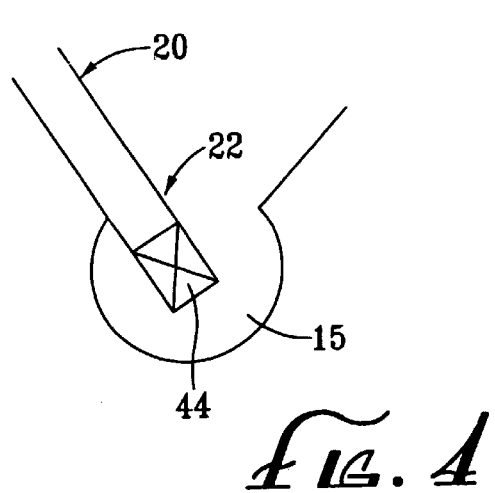
FIG. 4 depicts another embodiment of the filter having a turbine at a distal end of the aspiration catheter.

In another embodiment, distal end 22 of aspiration tube 20 includes turbine 44 as shown in FIG. 4. The turbine can be activated proximally to disintegrate or break up large embolic material to facilitate removal into lumen 25.

Figure 5:
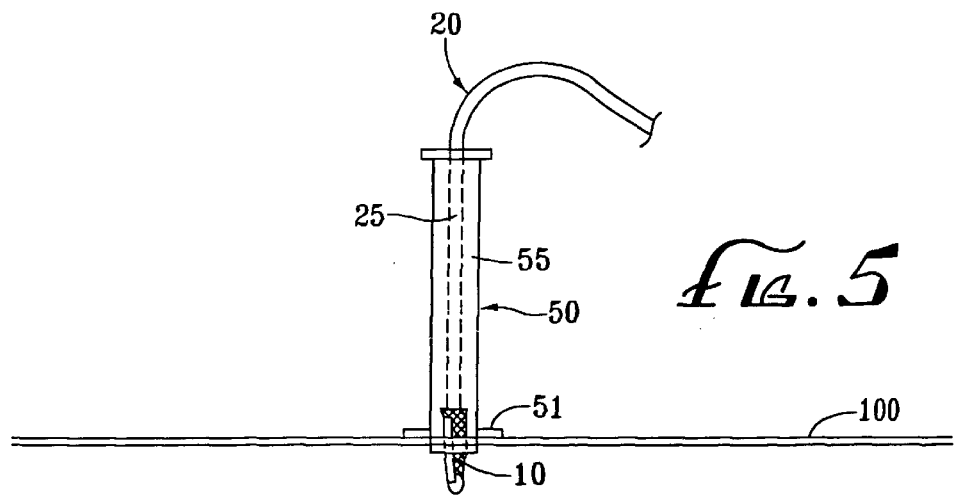
FIG. 5 depicts the filter of FIG. 1A passing through an introducer.

In using the filter and aspiration device of FIGS. 1A–1C, the filter can be introduced intravascularly directly through an open incision on the vessel. More preferably, the filter is placed in a collapsed state and inserted through lumen 55 of introducer 50 as depicted in FIG. 5. Introducer 50 is first introduced through an incision on vessel 100. Suture(s) may be placed on flange 51 to stabilize the introducer onto vessel 100. Filter 10 is then inserted into lumen 55 and deployed in the vessel. Aspiration tube 20 extends proximally within introducer 50 and is connected to a vacuum at its proximal end. The filter is expanded at its base which covers the perimeter of the vessel wall. The filter captures and the reservoir tip collects embolic material, e.g., air, fluid, thrombi, calcium, atheromatous plaque, and/or tissue debris, generated during the procedure. Emboli are aspirated into lumen 35 of aspiration tube 20 from the reservoir tip under negative pressure and removed. Emboli are also removed after the filter is collapsed and retrieved from introducer 50. In this way, removal of embolic material liable to cause distal embolization during cardiovascular procedures is maximized.

Figure 6:
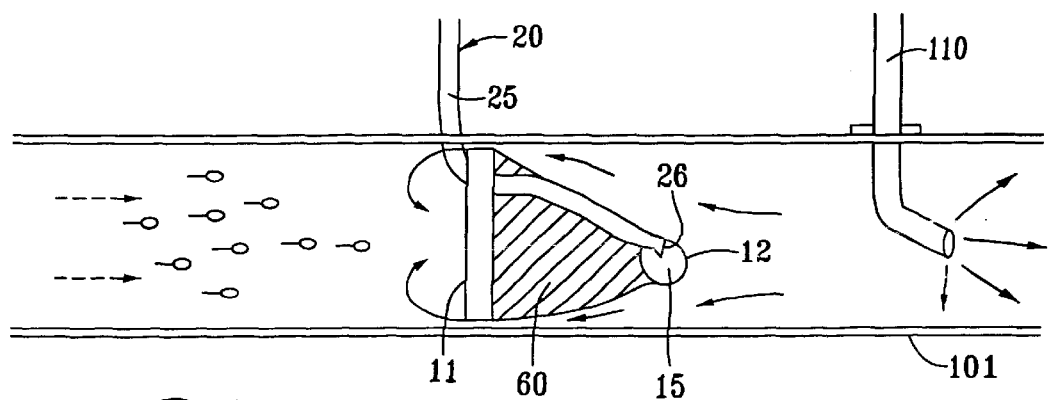
FIG. 6 depicts an occluder deployed in a vessel.

FIG. 6 depicts vessel occluding device 60 deployed in aorta 101. The occluder comprises a non-permeable or semi-permeable material arranged in a generally conical shape having expandable base 11 and vertex 12. Reservoir tip 15 is located at vertex 12 for collecting embolic material. Distal port 26 and lumen 25 of aspiration tube 20 communicates with tip 15. The device is most useful in cardiovascular surgeries requiring cardiopulmonary bypass during isolation of coronary arteries from the peripheral vascular circulation. Using occluding device 60 in place of an aortic clamp, injury to the aortic wall, such as dissection and hematoma, can be minimized.

In use, during cardiopulmonary bypass, for example, occluder 60 is placed in a collapsed state and introduced into aorta 101 upstream of the placement of aortic cannula 110. Occluder 60 is then expanded to occlude the aortic lumen. Oxygenated blood is infused, generally at approximately 3 to 4 liters/minute, through aortic cannula 110 downstream in aorta 101 to perfuse peripheral organs. Embolic material generated during cardiovascular surgery is collected in reservoir tip 15 of occluder 60. Since the heart is arrested during the procedure, pressure in the aorta distal to occluder 60 is higher than the pressure proximal to the occluder. As a result, blood flows from the high pressure side to the low pressure side, and in absence of aspiration, this reverse flow prevents the particles of emboli from reaching the filter, instead causing embolic particles to build up in the coronary arteries. With aspiration, however, blood and the embolic material are removed under vacuum through aspiration tube 20.

Occluder 60 is activated to provide aspiration at cross-clamp removal such that a slightly lower pressure would exist in the ascending aorta proximal to occluder 60 and distal to the region from where the cross-clamp was removed. Blood flows from the high pressure downstream portion of the aorta that is perfused by arterial return cannula 110 to upstream of occluder 60 because (1) small gaps are present between the vessel wall and the isolating filter/dam 60, and/or (2) the isolating filter/dam 60 is semipermeable. The permeable portion is designed to enhance flow into the ascending aorta proximal occluder 60, causing particles to be swept into the aspiration zone for removal. In another method, occluder 60 is non-permeable and cuffed with a balloon, thereby removing the need for a cross-clamp.

In another method, the proximal end of the aspiration tube is attached to a vacuum and an extracorporeal filter. In this way, blood or fluid is removed from the proximal aorta at a rate of 0.5 to 1 liter/min, is filtered free of debris, and is returned to the distal aorta through aortic cannula 110 at a rate of 3 to 4 liters/min, thereby minimizing blood loss.

Figure 7:
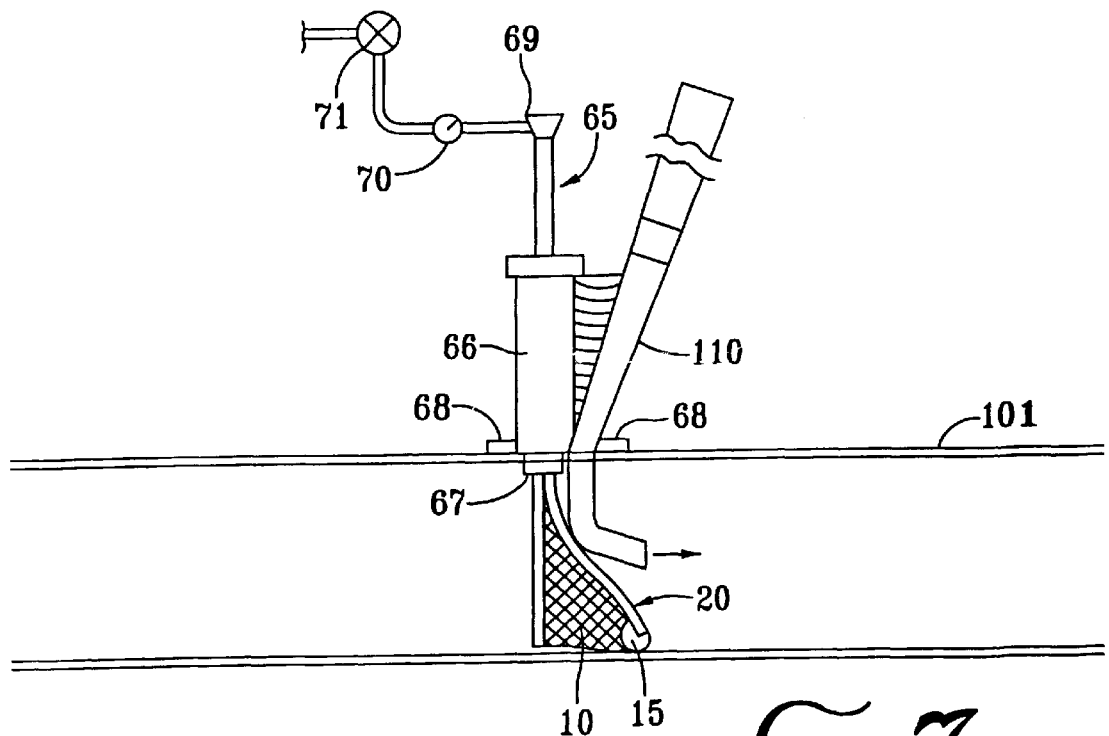
FIG. 7 depicts the filter of FIG. 1A mounted on a distal end of an insertion handle.

Filter 10 can be mounted on a distal end of insertion handle 65 and inserted into access lumen 66 of cannula 110 as depicted in FIG. 7. In use, cannula 110 and access port 67 are inserted through an incision on aorta 101. Suture(s) may be placed on flange 68 to secure the cannula onto aorta 101. Filter 10 in a collapsed state is inserted through access lumen 66 and deployed in the aorta. Aspiration tube 20 extends proximally within insertion handle 65 and is connected through proximal end 69 of the handle to pressure monitor 70, which is then connected to vacuum 71. The aspirated blood and fluid with the embolic debris from reservoir tip 15 can be passed through an extracorporeal filter and returned to a venous return cannula or arterial cannula 110.

Figure 8:
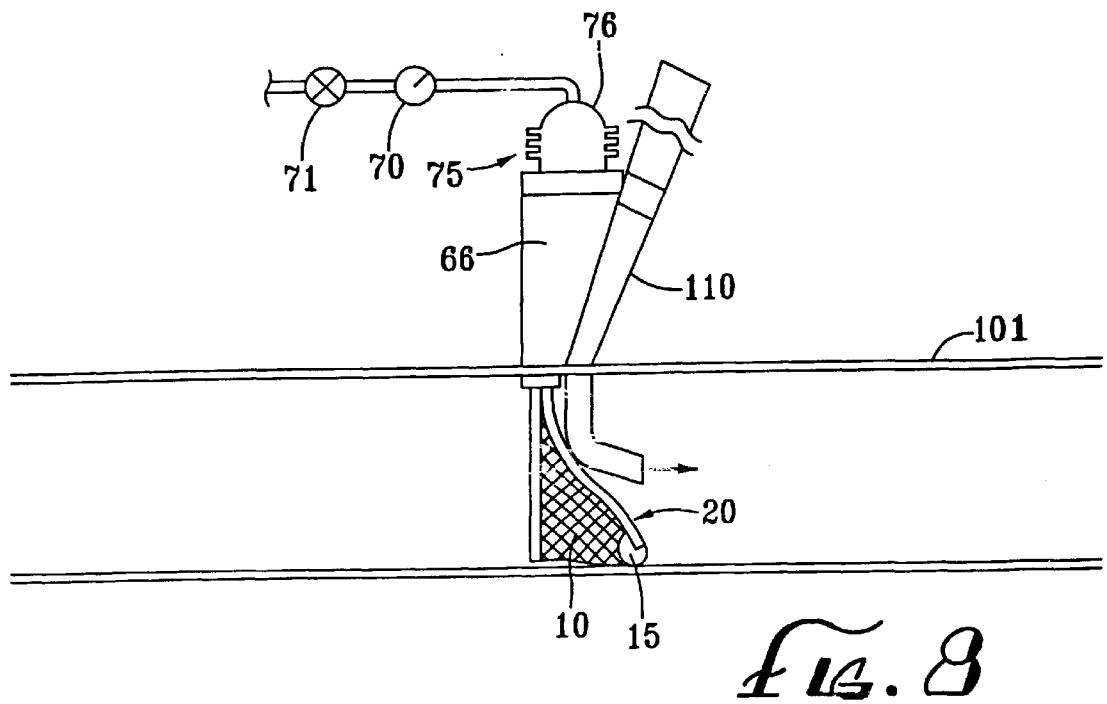
FIG. 8 depicts the filter of FIG. 1A deployed through an obturator.

The filter can also be deployed using obturator 75 as depicted in FIG. 8. Filter 10 is mounted on a distal end of obturator 75. The obturator carrying the filter in a collapsed state is inserted into access lumen 66 to deploy filter 10 in aorta 101. Aspiration tube 20 extends proximally within obturator 75 and is connected through proximal end 76 of the obturator to pressure monitor 70 and vacuum 71. After completion of cardiovascular procedures, vacuum is disconnected proximally, and obturator 75 is withdrawn, removing filter 10 and aspiration tube 20.

Figure 9:
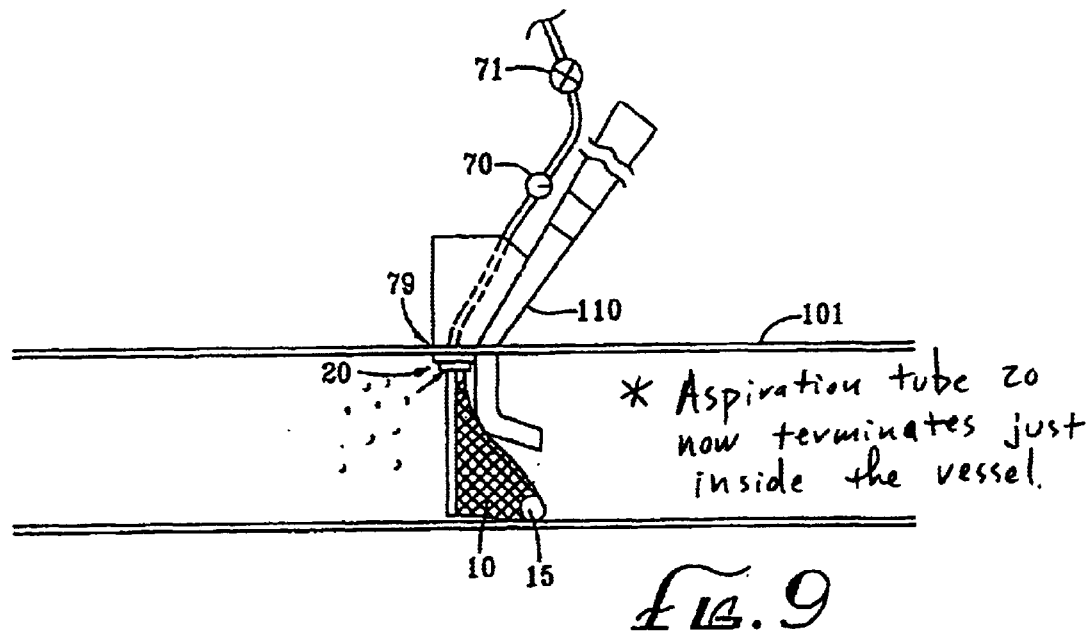
FIG. 9 depicts the filter of FIG. 1A mounted on a distal end of a cannula.

FIG. 9 depicts filter 10 mounted on distal end 79 of cannula 110. Aspiration tube 20 extends proximally within the cannula housing and is connected to pressure monitor 70 and vacuum 71. Alternatively, the aspiration tube may terminate just inside the vessel as shown also in FIG. 9. This embodiment applies as well to an aspiration tube carried by an obturator or the handle of a filter. In this manner, air emboli, which tend to rise within the vessel, will migrate close to the aspiration port and be removed.

By way of example, when the filter disclosed herein is intended for use in the aorta, the area of the mesh required for the device is calculated from Bernoulli's equation as described in our earlier applications including Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, filed Apr. 30, 1996, and Barbut et al., and U.S. application Ser. No. 08/645,762, filed May 14, 1996, all of which are incorporated herein by reference in their entirety.

In the embodiment of the filter that is to be used in the aorta, mesh with dimensions within the following ranges is desirable: mesh area is 0.5–10 $in^2$, more preferably 1–9 $in^2$, more preferably 2–8 $in^2$, more preferably 3–8 $in^2$, more preferably 4–8 $in^2$, more preferably 5–7 $in^2$; mesh thickness is 60–280 $\mu$m, more preferably 70–270 $\mu$m, more preferably 80–260 $\mu$m, more preferably 90–250 $\mu$m, more preferably 100–250 $\mu$m, more preferably 120–230 $\mu$m, more preferably 140–210 $\mu$m; thread diameter is 30–145 $\mu$m, more preferably 40–135 $\mu$m, more preferably 50–125 $\mu$m, more preferably 60–115 $\mu$m, more preferably 70–105 $\mu$m, and pore size is 500 $\mu$m or less, more preferably 400 $\mu$m or less, more preferably 300 $\mu$m or less, more preferably 200 $\mu$m or less, more preferably 100 $\mu$m or less, more preferably 50 $\mu$m or less and usually larger than at least a red blood cell. In a preferred embodiment of the invention, mesh area is 2–8 $in^2$, mesh thickness is 60–200 $\mu$m, thread diameter is 30–100 $\mu$m, and pore size is 50–300 $\mu$m. In a further preferred embodiment of the invention, mesh area is 3–5 $in^2$, mesh thickness is 60–150 $\mu$m, thread diameter is 50–80 $\mu$m, and pore size is 100–250 $\mu$m.

Figure 10:
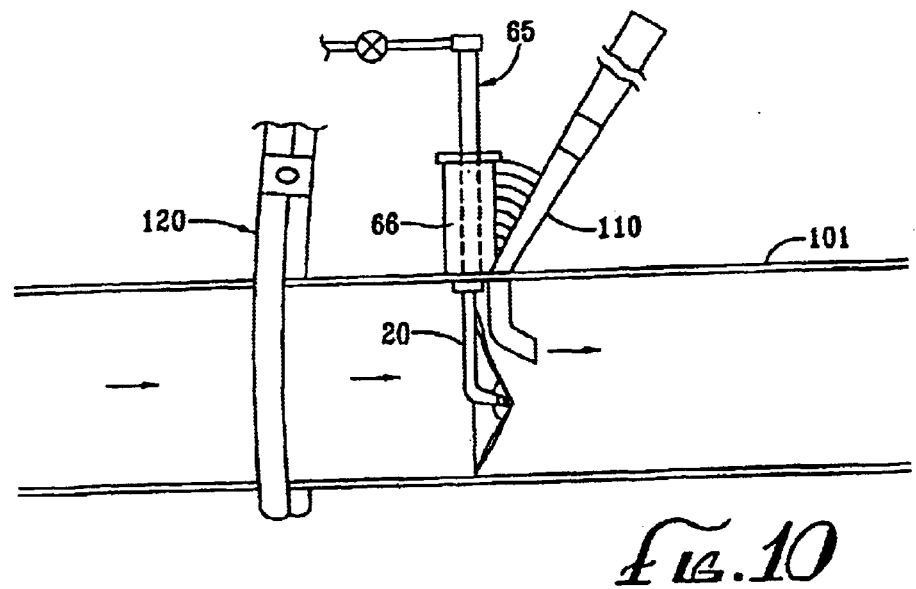
FIG. 10 depicts a dam deployed in the aorta during cardiopulmonary bypass.

During cardiovascular surgeries, it is known that distal embolization from embolic debris generated from the proximal aorta occurs during removal of aortic cross-clamping. Occluder or dam 60 mounted on a distal end of insertion handle 65 can be utilized to minimize embolic complications as depicted in FIG. 10. In use, dam 60 is inserted into access lumen 66 and deployed in aorta 101 shortly before discontinuation of cardiopulmonary bypass. When aortic cross clamp 120 is removed, aspiration through tube 20 is initiated and continued for approximately 30 seconds. In this way, blood and embolic material in the proximal aorta flow downstream into dam 60 and are aspirated and removed, thereby preventing embolization to peripheral organs. After aspiration, dam 60 is collapsed and removed from aorta 101 to re-establish blood flow.

The length of the aspiration catheter will generally be between 10 and 100 centimeters for aortic use, preferably approximately between 20 and 50 centimeters. The inner diameter of the catheter will generally between 0.2 and 2 millimeters, preferably approximately between 0.5 and 1 millimeter. The filter will be capable of expanding to an outer diameter of at least 0.2 centimeters, more preferably at least 0.5 centimeters, more preferably at least 1.0 centimeters, more preferably at least 1.5 centimeters, more preferably at least 2.0 centimeters, more preferably at least 2.5 centimeters, more preferably at least 3.0 centimeters, more preferably at least 3.5 centimeters, more preferably at least 4.0 centimeters, more preferably at least 4.5 centimeters, more preferably at least 5.0 centimeters. The filter will be capable of contracting to an outer diameter of between 0.05 and 2.0 millimeters, preferably approximately between 0.8 and 1.2 millimeters. These ranges cover suitable diameters for both pediatric and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. Moreover, it will be understood that each and every feature described for any given embodiment or in any reference incorporated herein, can be combined with any of the other embodiments described herein.

What is claimed is:

1. A filter, comprising:
   a porous material arranged in a generally conical shape having an expandable base and a vertex;
   an elongate member having a proximal end and a distal end attached to the expandable base of the porous material at a first circumferential location of the expandable base and extending perpendicularly from a central axis of the filter; and
   an aspiration tube having a proximal end, a distal end, and a lumen therebetween, the lumen communicating with a port at the distal end, the distal end of the aspiration tube communicating with an area at the first circumferential location of the expandable base.

2. The filter of claim 1, further comprising a reservoir tip located at the vertex of the cone for collecting filtered embolic material.

3. The filter of claim 2, wherein the reservoir tip comprises a nonporous material.

4. The filter of claim 3, wherein the reservoir tip comprises latex.

5. The filter of claim 4, wherein the latex covers a sector bounded by first and second radii and the included arc of a circle.

6. The filter of claim 1, further comprising a vacuum pump communicating with the proximal end of the aspiration tube.

7. The filter of claim 1, further comprising an infusion port in the area at the first circumferential location of the expandable base for infusion of saline.

8. The filter of claim 1, wherein the aspiration tube further comprises a turbine.

9. The filter of claim 1, wherein the filter is mounted on a cannula.

10. The filter of claim 9, wherein the aspiration tube extends proximally within the cannula.

11. The filter of claim 1, wherein the filter is mounted on an insertion handle.

12. The filter of claim 11, wherein the aspiration tube extends proximally within the insertion handle.

13. The filter of claim 1, wherein the aspiration tube extends proximally within an obturator.

14. A method for protecting a patient from embolization, comprising the steps of:
   inserting a filter into the patient's aorta, the filter comprising a porous material arranged in a generally conical shape having an expandable base and a vertex, an elongate member having a proximal end and a distal end attached to the expandable base of the porous material at a first circumferential location of the expandable base and extending perpendicularly from a central axis of the filter, and an aspiration tube having a proximal end, a distal end, and a lumen therebetween, the lumen communicating with a port at the distal end, the distal end of the aspiration tube communicating with an area at the first circumferential location of the expandable base;
   expanding the filter;
   aspirating emboli through the suction port, wherein embolic material is removed from the aorta; and
   collapsing the filter and removing the filter form the aorta.

15. The method of claim 14, further comprising the step of manipulating the aorta upstream of the filter.

16. The method of claim 14, further comprising the step of inserting an aortic cannula for perfusion of oxygenated blood.

17. The method of claim 16, further comprising the step of performing cardiopulmonary bypass.

18. The method of claim 14, further comprising the step of performing cardiac surgery.

19. The method of claim 14, wherein the filter further comprises a reservoir tip, and wherein the reservoir tip collects filtered embolic material.

20. The method of claim 14, wherein the aspiration tube extends proximally within an obturator.

* * * * *